United States Patent [19]

Wei

[11] Patent Number: 5,488,033

[45] Date of Patent: *Jan. 30, 1996

[54] TREATMENT TO REDUCE EDEMA

[75] Inventor: Edward T. Wei, Berkeley, Calif.

[73] Assignee: The Regents of the University of California, Oakland, Calif.

[ * ] Notice: The term of this patent shall not extend beyond the expiration date of Pat. No. 5,306,710.

[21] Appl. No.: 229,911

[22] Filed: Apr. 19, 1994

Related U.S. Application Data

[60] Continuation-in-part of Ser. No. 876,487, Apr. 30, 1992, Pat. No. 5,306,710, which is a division of Ser. No. 386,885, Jul. 28, 1989, Pat. No. 5,137,871.

[51] Int. Cl.$^6$ .................................... A61K 38/35
[52] U.S. Cl. .............................. 514/12; 530/306; 530/324
[58] Field of Search ............................... 514/12; 530/306, 530/324

[56] References Cited

U.S. PATENT DOCUMENTS

| | | | |
|---|---|---|---|
| 3,980,778 | 9/1976 | Ayer et al. | 514/171 |
| 4,404,198 | 9/1983 | Kelley | 424/230.1 |
| 4,415,558 | 11/1983 | Vale, Jr. et al. | 514/12 |
| 4,489,163 | 12/1984 | Rivier et al. | 514/12 |
| 4,517,181 | 5/1985 | Ling et al. | 514/12 |
| 4,528,189 | 7/1985 | Lederis et al. | 514/12 |
| 4,533,654 | 8/1985 | Lederis et al. | 514/12 |
| 4,579,844 | 4/1986 | Rovee et al. | 514/171 |
| 4,594,329 | 6/1986 | Vale, Jr. et al. | 514/12 |
| 4,605,642 | 8/1986 | Rivier et al. | 514/12 |
| 4,801,612 | 1/1989 | Wei | 514/12 |
| 5,137,871 | 8/1992 | Wei | 514/12 |
| 5,306,710 | 4/1994 | Wei | 514/12 |

OTHER PUBLICATIONS

Bernhagen et al., "MIF is a pituitary–derived cytokine that potentiates lethal endotoxaemia" Nature, vol. 365, 21 Oct. pp. 756–759 (1993).

Wei et al., "Peptides of the . . . Rat Pawskin," European Journal of Pharmacology, 168, pp. 81–86 (1989).

Chan et al., "Phospholipid Degradation and Edema Development in Cold–Injured Rat Brain", Brain Research, vol. 277, No. 2 (1983), pp. 329–337.

Esch et al., "Isolation and Characterization of the Bovine Hypothalamic Corticotropin–Releasing Factor", Biochem. & Biophy. Res. Comm., vol. 122, No. 3 (1984), pp. 899–905.

Ling et al., "Isolation and Characterization of Caprine Corticotropin–Releasing Factor", Biochem. & Biophy. Res. Comm., vol. 122, No. 3 (1984), pp. 1218–1224.

Melchiorri et al., "Action of Sauvagine on the Mesenteric Vascular Bed of the Dog", Regulatory Peptides, vol. 2, (1981), pp. 1–13.

Patthy et al., "Isolation and Amino Acid Sequence of Corticotropin–Releasing Factor from Pig Hypothalami", Proc. Natl. Acad. Sci. USA, vol. 82, No. 24, (1985), pp. 8762–8766.

Pinckard et al., "Platelet–Activating Factors", Inflammation: Basic Principles and Clinical Correlates, Gallin et al., eds., New York: Raven Press (1988), pp. 139–167.

Stern et al., "Ibuprofen in the Treatment of UV–B–Induced Inflammation," Arch. Dermatol., vol. 121, No. 4 (1985), pp. 508–512.

Primary Examiner—Jill Warden
Assistant Examiner—P. Lynn Touzeau
Attorney, Agent, or Firm—Majestic, Parsons, Siebert & Hsue

[57] ABSTRACT

Administration of a corticotropin-releasing factor (or a salt or analog thereof) decreases the leakage of blood components into tissues produced by various adverse medical conditions. Thus, treatments with corticotropin-releasing factor are useful in systemic inflammatory conditions.

5 Claims, 2 Drawing Sheets

CONTROL     INVENTIVE TREATMENT

CONTROL     INVENTIVE TREATMENT

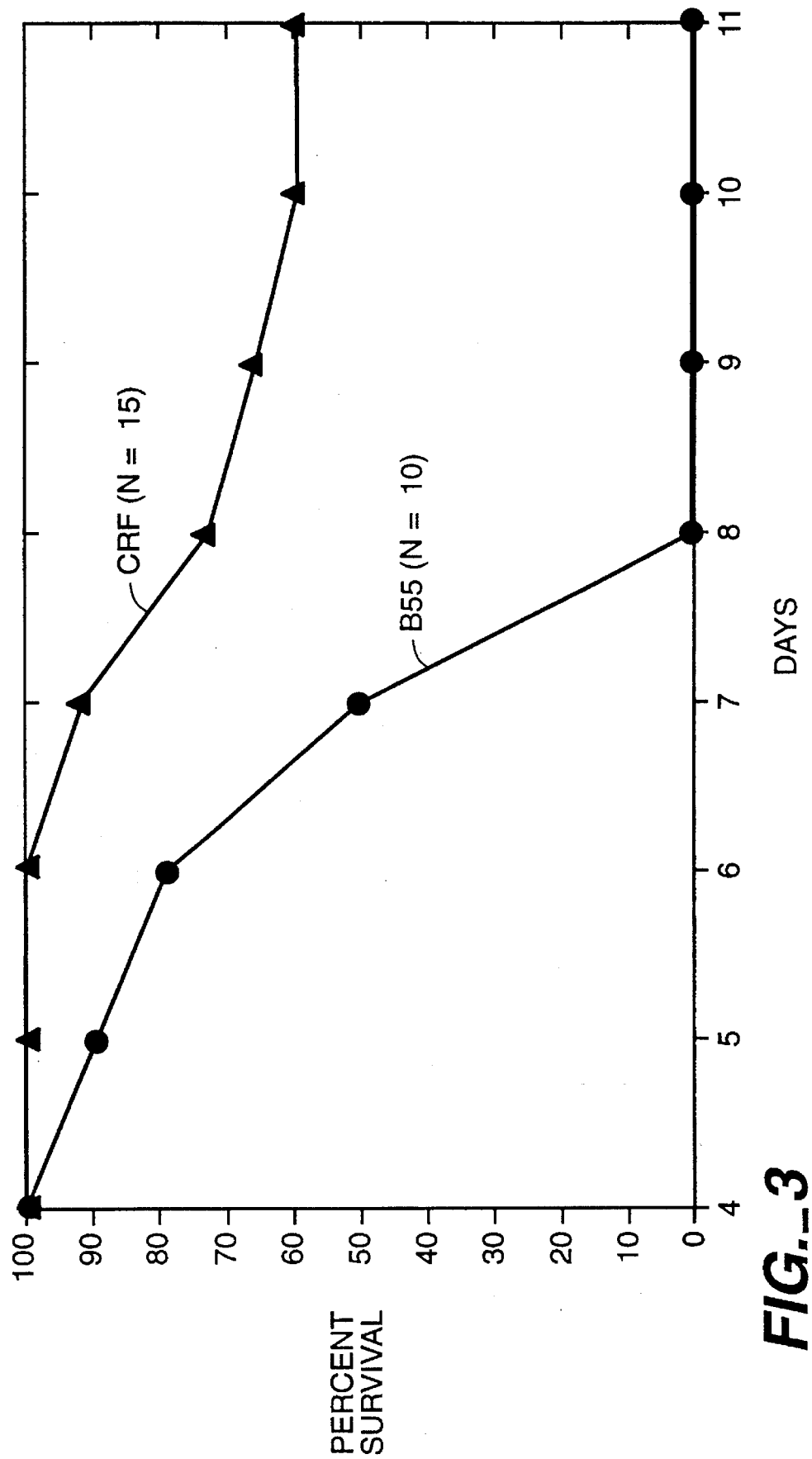
FIG._3

TREATMENT TO REDUCE EDEMA

This invention was made with Government support under Grant No. DA-00091 awarded by the National Institutes of Health. The Government has certain rights in this invention. This is a continuation-in-part of Ser. No. 07/876,487, filed Apr. 30, 1992, now U.S. Pat. No. 5,306,710, issued Apr. 26, 1994, which is a divisional of Ser. No. 07/386,885, filed Jul. 28, 1989, now U.S. Pat. No. 5,137,871, issued Aug. 11, 1992.

FIELD OF THE INVENTION

This invention generally relates to a method of reducing edema in connection with brain and musculature injuries, and more particularly to the use of corticotropin-releasing factor or its analogs in reducing edema of the brain and musculature following injury to or disease of these vascular beds and in treating severe inflammatory conditions, such as systemic inflammatory response syndrome, which results from e.g., sepsis, hemorrhagic shock, tissue injury.

BACKGROUND OF THE INVENTION

Inflammation is signaled by redness, swelling, heat, and pain as a reaction of the body against injury or assault. A variety of chemicals have been implicated as chemical mediators of the inflammatory reaction, including histamine, serotonin, kinins, prostaglandins, platelet-activating factors, leukotrienes, and, from nerve endings, substance P. Mediators of the acute inflammatory reaction seem to play roles in one or more of increasing vascular permeability, attracting leukocytes, producing pain, local edema, and necrosis.

A variety of physiologic responses occur from the biological events that constitute the inflammatory processes. For example, Pinckard et al. at Chapter 10 describe platelet-activating factors ("PAF") in the text *Inflammation: Basic Principles and Clinical Correlates* (Gallin et al. Ed., 1988). This family of structurally related compounds appear to promote a variety of physiologic actions that are directly or indirectly related to inflammatory reactions. The authors note that PAF has been implicated in the pathogenesis of human disease conditions such as endotoxin shock and organ transplantation rejection.

There are steroid and non-steroid, anti-inflammatory drugs known to the art. U.S. Pat. No. 4,579,844, inventors Rovee et al., issued Apr. 1, 1986, discloses topically treating an inflammatory condition of the skin by use of the prostaglandin synthetase inhibitor concurrently with a corticosteroid. U.S. Pat. No. 4,404,198, inventor Kelley, issued Sep. 13, 1983, discloses the topical application of a composition including phenyl salicylate to treat inflammation. U.S. Pat. No. 3,980,778, inventors Ayer et al., issued Sep. 14, 1976, discloses asteroid for use in the topical, oral or parenteral treatment of skin and mucous membrane inflammations. Ibuprofen (a known anti-inflammatory agent) has been tested in connection with UV-B-induced inflammation, but was found to have limited usefulness in treating sunburn reaction and is only somewhat more effective than placebo for the relief of symptoms associated with UV-B-induced inflammation after high dose UV-B phototherapy for psoriasis. Stern et al., *Arch. Derm.*, 121, pp. 508–512 (1985).

U.S. Pat. No. 4,801,612, inventor Wei, issued Jan. 31, 1989, discloses the use of inhibiting an inflammatory response in the skin or mucosal membranes of a patient by administering corticotropin-releasing factor, or its analogs.

However, the microcirculation for mammals has its own selective pharmacology for each particular vascular bed. This means that an anti-inflammatory agent useful in one vascular bed, such as the skin and mucosal membranes, cannot predictably be useful with other vascular beds, such as the brain or musculature. For example, histamine, bradykinin, serotonin, or arachidonic acid failed to increase permeability in blood vessels of the pia mater (the innermost vascularized covering of the brain), although these substances are potent edema producing agents in the skin and mucosa. Another example of selective pharmacology is epinephrine, since this endogenous substance constricts blood vessels in the skin but dilates blood vessels in skeletal muscle. Thus, the permeability characteristics of the blood vessels (particularly the post-capillary venules) in a vascular bed such as the brain are not equivalent to those in the skin and mucosa.

Corticotropin-releasing factor (hereinafter "CRF") is a 41 amino acid neuropeptide that is present in brain and the peripheral nerve endings, and stimulates ACTH release from pituitary cells. U.S. Pat. No. 4,489,163, inventors Rivier et al., issued Dec. 18, 1984, discloses rat CRF and its analogs. Human CRF has the same sequence as rat CRF.

There are a number of analogs of CRF known to the art. U.S. Pat. No. 4,415,558, inventors Vale, Jr. et al., issued Nov. 15, 1983, discloses the synthesis of sheep CRF, analogs, and isolation of the oCRF from ovine hypothalamic extracts. The synthetic OCRF was found to lower blood pressure.

A generally similar peptide, sauvagine, was described in Regulatory Peptides 2, 1–13 (1981). Sauvagine is a 40 amino acid peptide and has been reported to have biological activity in lowering blood pressure in mammals and stimulating the secretion of ACTH and β-endorphin.

U.S. Pat. No. 4,528,189, inventors Lederis et al., issued Jul. 9, 1985, and U.S. Pat. No. 4,533,654, inventors Lederis et al., issued Aug. 6, 1985, disclose peptides similar to the rat and sheep CRF and analogs thereof, and found this white sucker and carp urotensin respectively to stimulate ACTH and to lower blood pressure.

The other CRF-related peptide, white sucker urotensin, has an amino acid sequence the same as the carp urotensin, except the amino acid at the 24 position is isoleucine and the amino acid at the 27 position is glutamic acid.

Ling et al., *BBRC*, 122, pp. 1218–1224 (1984), disclose the structure of goat CRF, which is the same as that for sheep CRF. Esch et al., *BBRC*, 122, pp. 899–905 (1984), disclose the structure of bovine CRF which differs from sheep and goat CRF only by one amino acid residue (number 33 which is Asparagine rather than the number 33 Serine of goat and sheep CRF). Porcine CRF has been isolated and characterized by Patthy et al., *Proc. Natl. Acad. Sci.*, 82, pp. 8762–8766 (1985). Porcine CRF shares a common amino acid sequence (residues 1–39) with rat/human CRF and differs from these only in position 40 and 41. Residue 40 can be either asparagine or isoleucine and residue 41 is phenylalanine-amide.

SUMMARY OF THE INVENTION

In one aspect of the present invention, a method of treating a patient for a systemic inflammatory response syndrome comprises administering to the patient CRF (or a salt or analog thereof). Patients are treated for a systemic inflammatory response syndrome resulting from conditions such as sepsis.

Administration in accordance with the invention also reduces the permeability of brain and central nervous system blood vessels and is of therapeutic value in the treatment of brain and central nervous system injuries. Thus, for example, the serious medical emergency posed by brain edema, where the increased amounts of water compress and distort tissue architecture and impede delivery of oxygen to brain cells, can be substantially avoided or alleviated. Administrations in accordance with the invention also provide clinical benefits when used to limit or minimize leakage of blood constituents into tissue during surgery.

BRIEF DESCRIPTION OF THE DRAWINGS

FIG. 3 graphically illustrates the activity of corticotropin-releasing factor in the neutropenic rat model.

DETAILED DESCRIPTION OF THE PREFERRED EMBODIMENTS

Figure 1:
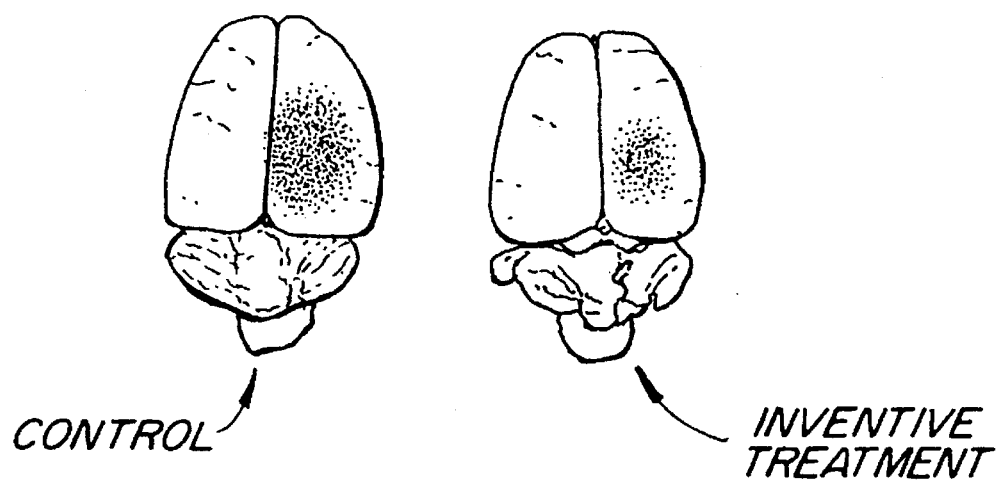
FIG. 1 shows two rat brains one hour after injury. The cortex stained with a blue dye (shown by shading, delineates the area of increased vascular permeability produced by cold injury. On the left is the brain of a rat treated with saline. On the right is the brain of a rat treated in accordance with the invention.

Systematic inflammatory response syndrome is the designation recently established by a group of researchers to describe related conditions resulting from, for example, sepsis, pancreatitis, multiple trauma such as injury to the brain, and tissue injury, such as laceration of the musculature, brain surgery, hemorrhagic shock, and immune-mediated organ injuries.

When an injury to the brain occurs, such as brain ischemia, or infarction, vasogenic edema occurs and the increased amounts of water compress and distort brain tissue architecture and impede the delivery of oxygen to brain cells. The patient can lose consciousness and stop breathing. I have discovered that CRF, its analogs, and related peptides (e.g., sauvagine and urotensin I) are effective in reducing the leakiness in the blood vessels of the brain (technically quantified as a change in vascular permeability) after injury. This discovery was surprising because the blood vessels of the brain, in contrast to the vessels found in the skin and mucosa, appear to have "tighter" junctions, and normally do not respond to the inflammatory mediators that promote leakage of blood vessels in the skin.

By "CRF" is meant herein mammalian corticotropin-releasing factor, including that isolatable from rat, human, beef, goat, pig, or sheep. Analogs of CRF include sauvagine, carp urotensin and sucker urotensin (all of which have been isolated from lower vertebrates), and those synthetic peptide structures analogous to CRF and disclosed in U.S. Pat. Nos. 4,415,558, 4,489,163, 4,553,654, and 4,528,189, incorporated herein by reference.

The effective neuropeptides for use in the present invention may be isolated from the above-noted natural sources or may be readily prepared synthetically, such as by solid phase peptide synthesis techniques. For example, the synthesis can be commenced from the carboxyl terminal end of the peptide by coupling the appropriate amino acid, e.g. L-arginine, L-isoleucine, L-phenylalanine or L-valine, to a suitable resin support, such as a p-methyl benzhydrylamine resin, a chloromethylated resin or a hydroxymethyl resin.

The coupling reaction may be carried out with the aid of a carboxyl group activating compound, such as dicyclohexylcarbodiimide, and with the α-amino group of the amino acid protected with a protecting group, such as t-butyloxycarbonyl (BOC), benzyl (BZL), p-methylbenzyl (MBZL), t-amyloxycarbonyl (AOC), tosyl (TOS), o-bromobenzyloxycarbonyl (BrZ), cyclohexyl (OHEX), or dichlorobenzyl ($BZLCl_2$). Following this coupling reaction, the α-amino protecting group is removed, such as by using trifluoroacetic acid in methylene chloride, trifluoroacetic alone or HCl in dioxane, with the deprotection being carried out at a temperature between about 0° C. and room temperature. Thereafter, each succeeding amino acid in the sequence is coupled in the same manner stepwise in the desired order, culminating in the addition of the final amino acid (e.g., L-serine, L-asparagine, or L-glutamine) to obtain the desired peptide.

As an alternative to adding each amino acid separately to the reaction, some may be coupled prior to addition to the solid phase reactor. Each protected amino acid or amino acid sequence is introduced into the solid phase reactor in excess (about a three- or four-fold excess), and the coupling may be carried in a medium of dimethylformamide:methylene chloride 1:1, or in dimethylformamide or methylene chloride alone. The success of the coupling reaction at each stage of the synthesis may be monitored by the ninhydrin reaction.

After the final amino acid in the sequence has been coupled, the deprotection step is carried out by treatment with a reagent such as hydrogen fluoride.

When a p-methyl benzhydryl amine resin has been used as the resin support, the peptide cleaved (by treatment with a reagent such as hydrogen fluoride) from the resin will be in the carboxyl terminal amide form. When a chloromethylated resin or a hydroxymethyl resin has been used as the resin support, the peptide cleaved from the resin support will be in the form of the carboxyl terminal benzyl ester, which may then be readily converted by methods well known in the art to provide the carboxyl terminal amide form of the peptide.

Therapeutically effective doses of CRF or its analogs in practicing this invention are at least about 0.01 μg/kg, more preferably from about 0.1 to about 200 μg/kg, and most preferably are from about 0.1 to about 50 μg/kg. A particularly preferred dose is about 1 to about 30 μg/kg administered i.v. or subcutaneously. The dose may be infused slowly intradermally or subcutaneously, or may be injected directly into an afflicted body part. When injected locally, doses of about 10 to about 100 μg per local administration (i.e. about 0.1 to about 1 μg/kg body weight) are preferred.

The neuropeptides should be administered under the guidance of a physician. Administration is preferably by intravenous, intradermal, or subcutaneous injection. Administration can be within about two weeks before or after injury, preferably about two hours before deliberate lacerations of the musculature, brain surgery, or the like, and preferably up to about three days after surgery or accidental injury. The drug is preferably delivered via the bloodstream, but local injections into the cerebrospinal fluid, brain, or into the muscle can be used for administration.

The active neuropeptide may be administered in combination with a pharmaceutically acceptable carrier, such as isotonic saline, phosphate buffer solution, or the like. Topical administration is not preferred, since CRF or an analog is a large molecule (e.g., 40 or 41 amino acids) and is not as efficiently delivered to the site of action as when administered by injection.

Although the peptides are generally water soluble as typically synthesized, they may be administered in the form of pharmaceutically acceptable non-toxic salts, such as acid addition salts. Illustrative acid addition salts are hydrochloride, hydrobromide, sulfate, sulphate, acetate, citrate, benzoate, succinate, malate, ascorbate, tartrate, or the like.

An in vivo model of injury to study brain edema has been developed as a reproducible edema model, which has the features of immediate cortical damage followed by the subsequent development of brain edema. This model is described by Chan et al., Brain Research, 277, pp. 329–337 (1983). The model uses rats which are anesthetized. A 2.5 cm incision is made over the sagittal suture and the bone of the right hemisphere exposed. A 60 mm$^2$ plate attached to a brass cup filled with dry ice-acetone mixture, with a temperature of −50° C., is applied to the rat skull for one minute. The animals are sacrificed at various intervals after the onset of cold-injury. A dye is administered intravenously before the freezing. Cortical slices are then obtained of the brain.

EXAMPLE I

Sixteen male rats were randomly divided into eight pairs and one rat in each pair received either saline or CRF (subcutaneously twice at 30 μg/kg, 30 min and 10 min before cold injury). The animals were anesthetized with sodium pentobarbital, 60 mg/kg intraperitoneally, and injected with Monastral blue, 60 mg/kg intravenously. A cold probe was applied onto the skull for four minutes and the brains taken out one hour after cold injury. The staining of brain tissues with Monastral blue, a colloidal pigment that gets trapped between the albuminal surface of the endothelial cell and the basement membrane, was proportional to the degree of vascular leakage. The results from the first pair are shown as FIG. 1. Table I summarizes the data.

TABLE I

| | CRF and Freeze Injury to Brain | | |
|---|---|---|---|
| Treatment | Area mm$^2$ | Intensity | Lesion Size |
| Saline | 43.4 ± 1.7 | 2.2 ± 0.04 | 96 ± 4 |
| CRF | 20.8 ± 1.2 | 2.0 ± 0.05 | 43 ± 3 |

The size of the lesion, measured as area in mm$^2$, and the degree of staining intensity, were quantified using an image-analysis software program called JAVA (Jandel Corporation, San Rafael, Calif.). The stain intensity, given in arbitrary units, was internally calibrated using Monastral blue solutions (1–30 mg/ml) placed on white filter paper. Values are mean ± S.E.M.

As can be seen visually from the shading of FIG. 1, the area and intensity of vascular permeability produced by cold injury was greatly less for the brain of a rat treated in accordance with the invention by administration of CRF than the brain of a rat treated with saline. As can be seen by the data of Table I, the lesion size of the CRF-treated group was only 44% that of the saline-treated group.

An observer, unaware of the rat's pretreatment and asked to distinguish between more damaged brains from the less damaged brain, is able to correctly guess 8 out of 8 times the assignment of the brains to either the saline or CRF group. Thus, the ability of CRF to suppress vascular leakage in the brain is shown.

EXAMPLE II

In a second set of experiments, the brain surface, namely the cerebral cortex, was injured by freezing and the water and sodium content were measured in the cerebral cortex and in the basal ganglia, a part of the brain away from the freeze zone. The water and sodium content of the brain tissue served as an index of brain edema. After freeze injury, the water and sodium content of the cerebral cortex were evaluated relative to non-frozen tissues. CRF administered in two separate doses of 30 μg/kg subcutaneously, one dose 15 minutes before the injury and the second dose 90 minutes after the first dose, inhibited the two indices of brain edema. Table II summarizes the data.

TABLE II

| TREATMENT | WATER CONTENT % | SODIUM mEq/kg dry wt |
|---|---|---|
| CEREBRAL CORTEX | | |
| Saline | 87 ± 0.2 | 310 ± 9 |
| CRF | 77 ± 4* | 271 ± 8* |
| BASAL GANGLIA | | |
| Saline | 75 ± 1 | 213 ± 4 |
| CRF | 76 ± 1 | 215 ± 9 |

Values are ± S.E.M., N = 5 animals per group
*P < .05 vs Saline Controls
Male Sprague-Dawley rats, 300–325 g, anesthetized with ketamine-acepromazine, were injected saline or CRF (30 μg/kg s.c. 2×) and injury to cerebral cortex was produced by applying a cold probe to the skull for 1 min. Brain tissues were obtained 3 hr later and analyzed for water and sodium content.

As can be seen from the data of Table II, the saline treated rats had increased water content at the cerebral cortex injury and substantially increased sodium with respect to the rats treated in accordance with the invention with CRF. That is, since the water and sodium content of the brain tissue served as an index of brain edema, the CRF treated rats were shown to have a suppressed vascular leakage due to cerebral cortex injury; however, the inventive treatment did not affect the water or sodium content in the non-injured basal ganglia.

EXAMPLE III

Figure 2:
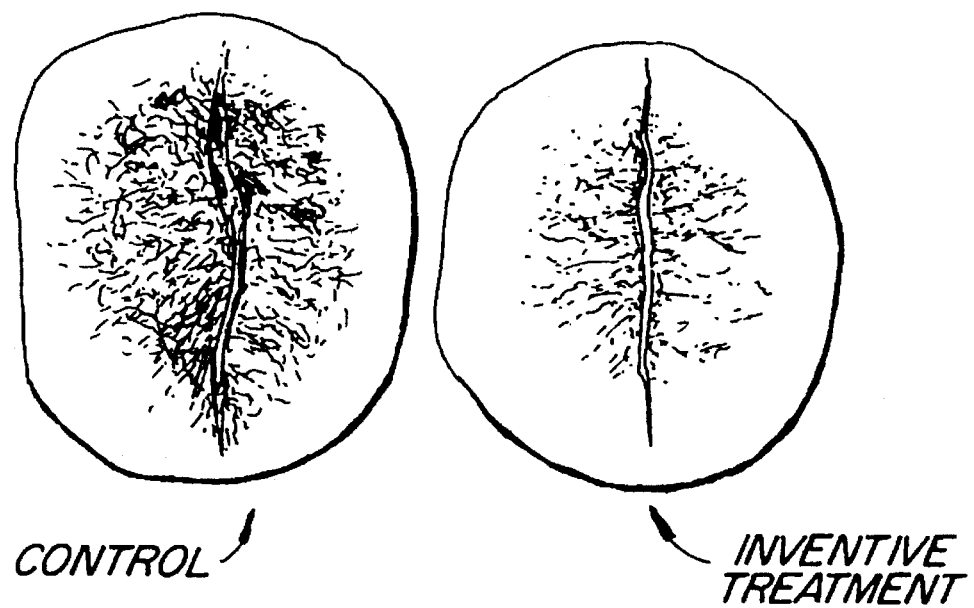
FIG. 2 shows two rat muscle tissue sections taken ½ hour after muscle injury (a 4 cm mid-line incision, or celiotomy). The tissue stained with a blue dye (shown by shading delineates the area of increased vascular permeability due to the surgical injury. On the left is the tissue of a rat treated with saline. On the right is the tissue of a rat treated in accordance with the invention.

Experiments were conducted on male Sprague-Dawley rats 243±15 gm (S.D., Simonsen Labs., Gilroy, Calif.) anesthetized with sodium pentobarbital, 60 mg/kg i.p. Monastral blue, 60 mg/kg i.v., was injected 0.2 ml/100 g, 3 minutes before a 4 cm midline incision through the abdominal muscle wall (celiotomy). Saline or CRF was administered to randomized pairs with N=8 rats per group. The size of the lesion, measured as area in mm$^2$, and its light intensity, were quantified using the JAVA image-analysis software program. The light intensity, given in arbitrary units, was internally calibrated using Monastral blue solutions (1–30 mg/ml) placed on white filter paper. Values are mean ± S.E.M. FIG. 2 illustrates the respective amount of vascular permeability for one pair of rats (control and treated). Tables III and IV set out data from these experiments.

TABLE III

Dose-Response Data for CRF and
Vascular Leakage After Celiotomy
CRF: injected at various doses subcutaneously 30 minutes
before a 4 cm midline incision, tissues taken 0.5 hour
after surgery.

| Treatment | Area mm² | Intensity | Lesion Size |
|---|---|---|---|
| Saline | 778 ± 34 | 2.1 ± 0.03 | 1624 ± 57 |
| CRF 15 µg/kg | 505 ± 16 | 2.0 ± 0.03 | 1031 ± 44 |
| CRF 30 µg/kg | 361 ± 18 | 1.9 ± 0.05 | 676 ± 47 |
| CRF 60 µg/kg | 257 ± 3 | 1.8 ± 0.05 | 468 ± 19 |

TABALE IV

Long Duration of CRF Before Surgery
CRF: 30 µg/kg s.c. injected 2 hour before a 4 cm
midline incision, tissues taken 0.5 hour after surgery

| Treatment | Area mm² | Intensity | Lesion Size |
|---|---|---|---|
| Saline | 735 ± 32 | 2.1 ± 0.02 | 1547 ± 62 |
| CRF | 477 ± 31 | 1.9 ± 0.03 | 919 ± 51 |

The celiotomy data illustrate the efficacious results from use of CRF in accordance with the invention as a result of musculature injury. Thus, the data of Table III show that vascular leakage was reduced in a dose dependent manner since the lesion size of the CRF-treated groups were 63%, 42%, and 29% that of the saline-treated group, respectively.

Table IV shows that CRF can be administered even two hours before musculature injury and still significantly reduce vascular leakage, since the lesion size of the CRF-treated group illustrated by Table IV was 59% that of the saline-treated group.

Increased vascular permeability occurs when blood vessels are exposed to toxic substances generated in injured tissues. These substances, called inflammatory mediators, include chemicals such as serotonin, substance P, bradykinin, neurotensin, inflammatory cytokines interleukin-1, tumor necrosis factor (TNF), and histamine. It has previously been shown that CRF will antagonize the edema-producing properties of these mediators when injected into the rat pawskin. These mediators act on blood vessels principally in the skin and mucosa.

For example, in the class of inflammatory mediators are those called platelet-activating factors (PAF), which act not only on blood vessels in the skin and mucosa, but also on small blood vessels in the lung and other visceral organs. PAF-acether is a prototype member of the PAF family. On a molar basis, PAF-acether is two to four orders of magnitude more potent than any other currently known vasoactive substance. PAF are rapidly synthesized by inflammatory cells when responding to injury and increase blood vessel permeability. PAF have been shown to be causally related to a variety of adverse medical conditions and may account for the pathologic and symptomatic processes of the disease state. For example, when bacteria are present in the bloodstream and produce toxins, the toxins stimulate the release of PAF and other factors, such as interleukin-1 and tumor necrosis factor, which then cause toxicity to endothelial cells lining the blood vessels resulting in increased vascular permeability throughout the various organs of the body, but especially the lung, and produce various conditions, such as multiple organ failure, pulmonary edema, and shock, which is manifested as a fall in blood pressure, blood volume, and hemoconcentration. Infection by the presence of bacteria in the bloodstream (a condition known as sepsis) is broadly viewed as a trigger for the generalized inflammation of the endothelial cells lining the blood vessels and this condition can also be caused by non-septic inflammatory conditions such as pancreatitis, ischemia, multiple trauma, and tissue injury, hemorrhagic shock, and immune-mediated organ injury. A group of researchers has recently established the designation "systemic inflammatory response syndrome" for use to describe these related conditions. (American College of Chest Physicians—Society of Critical Care Medicine Consensus Conference. Definitions for sepsis and organ failure and guidelines for the use of innovative therapies in sepsis. *Chest*, 101, pp. 1644–1655 (1992). The criteria for the clinical diagnosis of systemic inflammatory response syndrome have been described by R. C. Bone (*J. Amer. Med. Assoc.*, 268, pp. 3452–3455 (1992).)

Although one condition for which the invention is designed to treat is endotoxin shock, which is typically a gram-negative bacterial infection and is manifested as a fall in blood pressure, blood volume, and hemoconcentration, patients with severe systemic inflammatory response syndrome should not be assumed to have a gram-negative bacterial infection because a recent study suggests that less than half the patients in a comparative analysis of patient characteristics in four studies had bacteremia. Bone, *JAMA*, 268, pp. 3452– 3455 (Dec. 23/30, 1992).

Another condition in which PAF or other inflammatory mediators have been implicated is in the deterioration of organs after they have been removed from the body. This deterioration is a natural consequence of increased water permeation of healthy tissues.

Thus, an agent capable of antagonizing inflammatory mediators, such as PAF, will have therapeutic benefit in treating the severe inflammatory condition now sometimes designated as "systemic inflammatory response syndrome" and in the preservation of organs, such as for transplant of kidneys, heart, liver, and lungs, and for amputated limbs or digits prior to re-attachment to the body. In such uses the vasculature of the organs to be transplanted are preferably perfused with a solution containing about 5 to about 500 µg of CRF or CRF analogs.

The data of Table V shows that the increased vascular permeability produced by PAF-acether is antagonized by CRF.

TABLE V

CRF Inhibits Vascular Leakage Produced by PAF-Acether
CRF: 30 µg/kg s.c. injected 30 minutes before subcutaneous
injection of PAF-acether (1 µg/0.1 ml/rat) into the abdomen;
muscle removed 0.5 hour later.

| Treatment | Area mm² | Intensity | Lesion Size |
|---|---|---|---|
| Saline | 327 ± 22 | 1.8 ± 0.04 | 589 ± 43 |
| CRF | 188 ± 16 | 1.4 ± 0.05 | 260 ± 26 |

The muscle lesion size of the CRF-treated group was 44% that of the saline-treated control group, illustrating the beneficial use of the invention in conditions such as where patients are experiencing endotoxin shock due to PAF.

EXAMPLE IV

The neutropenic rat model of sepsis, designed to mimic the systemic inflammatory response syndrome in humans, is described by Collins et al. from *The Journal of Infectious Diseases*, 159:6 (June 1989) and *The Journal of Clinical Investigation*, 88:885 (September 1991). The white blood cells of rats are artificially decreased and then the animals are infected with the bacteria Pseudomonas. The animals die from overwhelming infection within 7 to 9 days of infection and examination of the tissues with histological and pathological techniques reveal the characteristic organic manifestations of the systemic inflammatory response syndrome, namely, organ edema and tissue necrosis.

In a typical experiment, 10 rats serving as controls received saline and 15 rats received CRF at a dose of 100 µg/kg intravenously, given twice a day for four days after the onset of fever. At the end of 8 days, all of the animals in the control group were dead (100% mortality). By contrast, 60% (9/15) of the CRF group were still alive at day 11 when the experiment was concluded. The difference between the saline and CRF treated groups were statistically significant ($P < 0.002$). This data is illustrated by FIG. 3, where the vertical axis is percent survival and the horizontal axis is days.

It is to be understood that while the invention has been described above in conjunction with preferred specific embodiments, the description and examples are intended to illustrate and not limit the scope of the invention, which is defined by the scope of the appended claims.

It is claimed:

1. A method of treating a patient suffering from a systemic inflammatory response syndrome characterized by vascular leakage, comprising:

administering to the patient an amount of a corticotropin-releasing factor effective to suppress vascular leakage.

2. The method as in claim 1 wherein the amount administered is at least about 1 µg/kg of patient body weight and blocks the actions of one or more inflammatory mediators.

3. The method as in claim 1 wherein the administering is by intravenous, intradermal or subcutaneous injection.

4. The method as in claim 3 wherein the corticotropin-releasing factor is administered in combination with a pharmaceutically acceptable carrier.

5. The method as in claim 1 wherein the administering is an injected or infused dose of between about 1 to about 100 µg/kg of patient body weight.

* * * * *